(12) United States Patent
Gottschalk et al.

(10) Patent No.: US 10,933,023 B2
(45) Date of Patent: Mar. 2, 2021

(54) PARTICLE CONTAINING AT LEAST A VOLATILE SUBSTANCE AND PROCESS FOR ITS PREPARATION

(71) Applicant: Erber Aktiengesellschaft, Getzersdorf bei Traismauer (AT)

(72) Inventors: Pia Gottschalk, Krems (AT); Eva-Maria Binder, Tulln (AT); Franz Waxenecker, Mank (AT); Carina Schieder, Hartberg (AT); Anne-Christine Hunger, Munich (DE); Stephen Charles John Cole, Würmla (AT)

(73) Assignee: ERBER AKTIENGESELLSCHAFT, Getzersdorf Bei Traismauer (AT)

( * ) Notice: Subject to any disclaimer, the term of this patent is extended or adjusted under 35 U.S.C. 154(b) by 0 days.

(21) Appl. No.: 16/334,034

(22) PCT Filed: Sep. 19, 2017

(86) PCT No.: PCT/EP2017/001111
§ 371 (c)(1),
(2) Date: Mar. 18, 2019

(87) PCT Pub. No.: WO2018/059732
PCT Pub. Date: Apr. 5, 2018

(65) Prior Publication Data
US 2019/0269622 A1    Sep. 5, 2019

(30) Foreign Application Priority Data

Sep. 30, 2016 (EP) ...................... 16450024

(51) Int. Cl.
| | |
|---|---|
| *A61K 9/50* | (2006.01) |
| *A23K 40/30* | (2016.01) |
| *A61K 9/48* | (2006.01) |
| *A61K 31/015* | (2006.01) |
| *A61K 31/05* | (2006.01) |
| *A61K 31/085* | (2006.01) |
| *A61K 31/11* | (2006.01) |
| *A61K 31/122* | (2006.01) |
| *A61K 31/618* | (2006.01) |
| *A61K 36/23* | (2006.01) |
| *A61K 36/235* | (2006.01) |
| *A61K 36/45* | (2006.01) |
| *A61K 36/53* | (2006.01) |
| *A61K 36/534* | (2006.01) |
| *A61K 36/54* | (2006.01) |
| *A61K 36/61* | (2006.01) |
| *A61K 36/752* | (2006.01) |
| *A61K 36/88* | (2006.01) |
| *B01J 13/04* | (2006.01) |
| *A61Q 19/00* | (2006.01) |
| *A23L 27/00* | (2016.01) |
| *A61K 8/92* | (2006.01) |
| *A61K 8/02* | (2006.01) |

(Continued)

(52) U.S. Cl.
CPC .............. *A61K 9/501* (2013.01); *A23K 40/30* (2016.05); *A23L 27/72* (2016.08); *A61K 8/0283* (2013.01); *A61K 8/25* (2013.01); *A61K 8/922* (2013.01); *A61K 9/145* (2013.01); *A61K 9/485* (2013.01); *A61K 9/4875* (2013.01); *A61K 9/50* (2013.01); *A61K 9/5015* (2013.01); *A61K 9/5089* (2013.01); *A61K 31/015* (2013.01); *A61K 31/05* (2013.01); *A61K 31/085* (2013.01); *A61K 31/11* (2013.01); *A61K 31/122* (2013.01); *A61K 31/618* (2013.01); *A61K 36/23* (2013.01); *A61K 36/235* (2013.01); *A61K 36/45* (2013.01); *A61K 36/53* (2013.01); *A61K 36/534* (2013.01); *A61K 36/54* (2013.01); *A61K 36/61* (2013.01); *A61K 36/752* (2013.01); *A61K 36/88* (2013.01); *A61Q 19/00* (2013.01); *B01J 13/04* (2013.01); *A61K 2800/10* (2013.01); *A61K 2800/621* (2013.01)

(58) Field of Classification Search
CPC ...... A61K 36/752; A61K 8/0283; A61K 9/50; A61K 9/5015
See application file for complete search history.

(56) References Cited

U.S. PATENT DOCUMENTS

| | | | |
|---|---|---|---|
| 4,707,367 A | 11/1987 | Miller et al. | |
| 5,256,386 A * | 10/1993 | Nystrom | ................ B01J 20/103 423/338 |

(Continued)

FOREIGN PATENT DOCUMENTS

| | | | | |
|---|---|---|---|---|
| EP | 1 419 811 A1 | 5/2004 | | |
| EP | 1419811 A1 * | 5/2004 | ............ | B01J 13/043 |

OTHER PUBLICATIONS

EP-1419811-A1 (Espacenet English Translation, downloaded in May 2020) (Year: 2020).*

(Continued)

*Primary Examiner* — Mark V Stevens
(74) *Attorney, Agent, or Firm* — Jacobson Holman PLLC

(57) ABSTRACT

The invention is directed to a particle containing at least a volatile substance comprising a core comprising at least one matrix material and the at least one volatile substance and at least one coating layer, whereby a first coating layer is a non-confluent layer comprising at least a carrier material, whereby optionally the non-confluent layer contains at least one hydrophobic substance, and optionally the particle is surrounded by at least one confluent layer and/or further non-confluent layer(s) as well as to a process for producing the same.

17 Claims, 5 Drawing Sheets

(51) Int. Cl.
*A61K 8/25* (2006.01)
*A61K 9/14* (2006.01)

(56) References Cited

U.S. PATENT DOCUMENTS

2003/0215496 A1* 11/2003 Patel .................. A61P 9/04
424/452
2011/0142985 A1 6/2011 Meunier et al.

OTHER PUBLICATIONS

Elia et al (J Coat Technol Res, 2015, vol. 12, pp. 793-799) (Year: 2015).*
International Search Report, dated Jan. 1, 2018 (7 pages).

* cited by examiner

PARTICLE CONTAINING AT LEAST A VOLATILE SUBSTANCE AND PROCESS FOR ITS PREPARATION

BACKGROUND OF THE INVENTION

The present invention is directed to a particle containing at least a volatile substance and to a process for its preparation. The particle consists of a core comprising at least one matrix material and the at least one volatile substance as well as at least one coating layer.

It is known to incorporate active ingredients such as plant extracts, pharmaceuticals or also essential oils into granules, comprising in their core at least a matrix material, which is able to adhere to or take up or matrix encapsulate the active ingredients. To avoid that the active ingredients are destroyed or evaporated during further storage or processing, for example, conditioning, pelletizing or granulation of an animal feed or feed additive, the core granules can have at least one coating applied by fluidized bed processing, especially fluidized bed drying or other coating technique known in the art. Thereby one can obtain particles or microparticles consisting of a core and a confluent coating layer. However, it is not possible to protect the volatile active ingredients in the particle, especially these present in the core during the application of such a coating layer. The volatile active ingredient(s) is (are) destroyed or escape during preparation of the coating by the fluidization process even at relatively low processing temperatures. Such losses during the process or storage are expensive and result in an uncertainty of the amount of volatile active ingredient contained in the product. Furthermore, there is a risk of insufficient loading of the particle with the desired volatile compound.

From US 2011/0142985 one can gather a granular feed additive with a core and coating whereby the core is a microparticle composed of at least one active plant extract and/or at least a flavouring incorporated in a matrix. The coating comprises at least one sweetener and optionally at least one potentiator and at least one flavouring. A flavouring according to US 2011/0142985 is any flavouring as defined by European Directive 88/388/EEC. Moreover this document also shows a process for preparing the granular feed additive.

U.S. Pat. No. 4,707,367 describes a melt-based and extruded solid essential oil composition in particulate form having a hydrophilic core consisting of sugar, starch hydrolysate, a selected emulsifier, essential oil flavour and water, whereby the essential oil flavour is provided in a substantially completely encapsulated form.

EP 1 419 811 A1 is directed to stable plant extracts which are provided in a microencapsulated manner. The microcapsules are prepared by preparing an emulsion containing water, a solubilizer, natural polymers and the substance to be encapsulated and than spray drying of this emulsion will give the requested powdery microcapsules.

SUMMARY OF THE INVENTION

The present invention aims therefore to a particle and a process for its preparation which particle has a core containing at least one volatile substance, especially high contents of the at least one volatile substance and at least one coating layer protecting the volatile substance in the particle in such a manner that nearly no loss of the same results during preparation, further processing and storage of the particle occurs. Moreover the particle should be easy to handle and should be an especially free-flowing particle which is not sticky and does not go lumpy.

This objective has been achieved by providing a particle having a core comprising at least one matrix material and at least one volatile substance and at least one coating layer which particle is characterized in that
a) the matrix material is selected from the group of fats, hydrogenated triglycerides and waxes that are solid or semi-solid at 20° C. and 1 atmosphere,
b) the core contains 30% by weight to 97% by weight of matrix material based on the total mass of the core,
c) the at least one volatile substance being contained in the core has a vapor pressure at 125° C. between 10 mm Hg and 200 mm Hg,
d) a first coating layer is a non-confluent layer comprising at least a carrier material being attached to the core,
e) the carrier material is an inorganic material having a porous structure and a D50 of 1 to 300 µm,
f) the core has an average surface coverage by the non-confluent layer of 1% to 50%
whereby optionally the non-confluent layer contains at least one hydrophobic substance, and optionally the particle is surrounded by at least one confluent layer and/or further non-confluent layer(s),
whereby the presence of the first non-confluent layer increases the recovery of the volatile substance in the core during granulation or fluidization of the particle.

By providing a particle having a first coating layer which is a non-confluent layer preferably comprising at least one hydrophobic substance it is surprisingly possible to avoid evaporation of the at least one volatile substance contained in the core irrespectively whether this particle is stored for a long time or further processed at higher temperature. A stable and durable particle is obtained, if the core contains 30% by weight to 97% by weight of matrix material based on the total mass of the core. By providing a core containing up to 97% by weight of matrix material it is possible to adjust the durability and compactness of the core according to the respective requirement and at the same time to control the coverage obtained with the non-confluent layer. Especially good results are obtained if the at least one matrix material of the core is selected from the group of fats; hydrogenated triglycerides and waxes that are solid or semi-solid at 20° C. and 1 atmosphere. Moreover it is possible to use the particle obtained in a standard granulation or fluidization procedure without loss of more than 20%, preferably 10%, most preferred 5% by weight of the volatile substance contained in the core. Thus an increased recovery of the volatile substances in the core, preferably more than 10%, more than 20%, more than 30% and more than 50% is achieved.

An especially good retainment of the volatile substance in the core is obtained if inorganic carrier materials having a porous structure having a $D_{50}$ of 1 to 300 µm. Preferably inorganic carrier materials having a porous structure having a $D_{50}$ of 2 to 150 µm and more preferably of 5 to 30 µm can be used as the carrier material. The $D_{50}$ is defined as the particle size (diameter) below which 50% of the particles of a sample are. With such carrier material it is possible to obtain a non-confluent layer having a sufficient thickness for being able to absorb volatile substances being present in the core and at the same time to obtain a particle having a non-confluent layer covering not more than 50% of the surface of the core.

It is assumed that by choosing the matrix material of the core as well as the volatile substance in such a way that the carrier material of the first non-confluent layer adheres only on molecules of the volatile substance being exposed at the surface of the core, a core is obtained being only covered to a small to medium amount with the carrier material of the first non-confluent layer. If for example the volatile substance or also the mixture of volatile substances which is/are preferably liquid at a room temperature of 20±5° C. the carrier material of the first non-confluent layer is bound by liquid bridges at regions of the core material exposing the volatile substance(s) at the surface. A bonding between the matrix material and the carrier material will surprisingly not take place and therefore also a coverage of the core material in regions without any volatile substance at the surface will not take place, so that a particle is obtained having a core and at least one non-confluent layer covering at most 50% of the core, especially at most 25% and most preferably at most 15% of the surface of the core. Preferably a particle is obtained having an average surface coverage by the non-confluent layer of 2% to 25% and most preferably of 3% to 15%.

The particles obtained can be used in nutrition for example for introduction of any flavouring agent in feed or food, for addition of volatile active ingredients in pharmaceutical products or feed and food. Naturally it is possible to use the particles as such as a food or feed additive by mixing the same in feed or feed premixes or in convenience food products such as for example chewing gums. Furthermore they can be used for introducing flavourings in toiletries, in cleaning and washing liquids and/or powders but also as a curing and/or supporting agent in different products.

Preferably the core contains 3% by weight to 50% by weight, preferably 5% by weight to 40% by weight and even more preferably 10% by weight to 30% by weight volatile substances based on the total mass of the core. By choosing the amount of volatile substance in this range it is possible to obtain a stable core particle containing an amount of volatile substance which is fixedly attached to the core, especially adsorbed or absorbed at the surface of the core material or also embedded in the matrix material forming the core and the volatile substance can also be bound to the material of the non-confluent layer and therefore any loss especially any evaporation of the volatile substance during any further processing of the particle can be avoided.

Excellent results can be obtained if the at least one volatile substance being contained in the core has a vapor pressure at 125° C. between 10 mm Hg and 200 mm Hg, preferably between 30 mm Hg and 70 mm Hg. The vapor pressures being calculated using the Antoine equation and constants obtained from Yaws, C. L. & Satyro, M. A., "Chapter 1—Vapor Pressure—Organic Compounds", in "The Yaws Handbook of Vapor Pressure (Second Edition) Antoine Coefficients", Elsevier B. V. (2015) pp 1-314, ISBN: 978-0-12-802999-2. An alternative source obtaining Antoine constants may be Dykyj, J., Svoboda, J., Wilhoit, R. C., Frenkel, M. & Hall, K. R., Chapter 2 Organic Compounds, C1 to C57 Part 2, in Vapor Pressure and Antoine Constants for Oxygen Containing Organic Compounds, Springer Materials (2000) pp 111-205. ISBN: 978-3-540-49810-0. In case the different vapor pressure calculations result in contradictory results it is herein preferred that the vapor pressure of the at least one volatile substance in the core is preferably in the range starting from the vapor pressure of D-limonene (CAS-No: 5989-27-5) and ending at the vapor pressure of eugenol (CAS-No: 97-53-0), more preferred in the range starting from the vapor pressure of linalool (CAS-No: 78-70-6) and ending at the vapor pressure of D-carvone (CAS-No: 2244-16-8).

Such substances can surprisingly be retained in the core of the particle by the non-confluent layer being attached to the surface of the core. It is assumed that the non-confluent layer chosen is able to attract evaporating molecules of the volatile substance and binding the same by a physical bond whereby evaporation of the volatile molecules contained in the core out of the particle is avoided.

By selecting the at least one volatile substance being contained in the core from an essential oil or a plant extract both being preferentially prepared from a plant selected from the group of oregano, thyme, wintergreen, caraway, mint, peppermint, anise, orange, lemon, fennel, star anise, clove, cinnamon and garlic; or from an ingredient, component or compound of the essential oil or plant extract, which also may be derived from synthetic or biotechnological production, preferably selected from the group of D-limonene, γ-terpinene, p-cymene, 2-carene, linalool oxide, isomenthone, camphor, linalool, terpinen-4-ol, 2-isopropyl-1-methoxy-4-methylbenzene, L-menthol, ethylamine, α-terpineol, β-caryophyllene, D-carvone, methyl salicylate, α-caryophyllene, lavandulyl acetate, caryophyllene oxide, eugenol, thymol and carvacrol; the recovery rates of the volatile substances are very high. The particle containing a volatile substance as defined can especially be used as flavoring in human or animal nutrition, anti-bacterial, anti-inflammatory, anabolic, morphology improving, gut integrity enhancing, digestibility improving, gut microbiota modulating, gut health status supporting agent, as digestibility enhancer to allow improved feed utilization and sparing of nutrients; as tool to decrease evaporation and to improve heat stability of the particle containing volatile substances, especially essential oils during feed and fool conditioning, pelleting, extrusion and any drying process such as spray drying and/or roller-drying and/or pasteurization; as prevention and/or curing agent for humans or animals suffering from gastro-intestinal tract related diseases such as diarrhea, intestinal enteritis and so on, as flavoring agents for chewing gums to enhance the refreshing experience of a chewing gum, as flavoring for toiletries to have a boosting flavoring effect in any kind of toiletries such as shower gel, shampoo, tooth paste, deodorants and so on, as flavoring and substances with antibacterial efficacy in cleaning and washing formulations based on a liquid and/or dry solution and many other applications.

Herein essential oils are defined as substances that are prepared according to at least one procedure described in the European Pharmacopoeia, 8th Edition, supplement 8.0/2098.

Herein plant extracts are defined as substances that are prepared according to at least one procedure described in the European Pharmacopoeia, 8th Edition, supplement 8.5/0765.

All compounds mentioned can be either of natural, synthetic or biotechnological origin.

Preferably, the volatile substance or also a mixture of different volatile substances being contained in the core is liquid at a temperature of 20±5° C. whereby it is assured that the volatile substance in the core forms a non-confluent layer with the at least one carrier material of the non-confluent layer. Furthermore, it is possible that the volatile substance is a sensory active substance such as an olfactory active substance influencing the smell, a gustatory active substance influencing the taste or a substance influencing both the smell and the taste like aromas or flavors.

It is possible that the volatile substance is an aliphatic compound, an ester, an acid, an alcohol, an aldehyde, a ketone or derivatives thereof, especially a terpene such as open chain terpenes, cyclic terpenes, monoterpenes or sesquiterpenes; especially a lactone like γ-octalactone, γ-nonalactone, γ-decalactone or γ-undecalactone.

The volatile substance can also be an aromatic compound especially a benzoic acid derivative, a phenol derivative, a phenylpropane derivative or a coumarin derivative.

Particles which have according to a further development of the invention a diameter of the core between 50 μm and 1000 μm, preferably between 100 μm and 300 μm and even more preferably between 175 μm and 225 μm are sufficiently small for being mixed and evenly distributed in liquid, pasty or also solid products like powders or granules. It is therefore possible to use only small amounts of the particle in products for obtaining the effect chosen, being an increased recovery of the volatile substances in the core, preferably by more than 10%, more than 20%, more than 30%, more than 50%. It is possible for example to add the particle in incorporated amounts of 0.01 g to 7 kg per 1000 kg and/or 1000 l to prevention and/or curing agents for humans or animals, in incorporated amounts of 0.01 g to 10 kg per 1000 kg and/or 1000 l to flavoring agents for human or animal nutrition or also added in amounts of 10 g to 10 kg per ton to feed/dry milk replacers and/or per 1000 l of water/milk in feed, milk replacers and also to water.

A stable and durable particle is especially characterized in that the core contains, preferably 50% by weight to 85% by weight and even more preferably 58% by weight to 70% by weight of matrix material based on the total mass of the core. By providing a core containing up to 85% by weight of matrix material it is possible to adjust the durability and compactness of the core according to the respective requirement and at the same time to control the coverage obtained with the non-confluent layer. The more matrix material is present in the core the smaller is the coverage of the core with the non-confluent layer.

Especially good results can be obtained if the at least one matrix material of the core is selected from hydrogenated triglycerides, preferably vegetal triglycerides like palm oil, sunflower oil, corn oil, rapeseed oil, peanut oil or soybean oil or from waxes, preferably candelilla wax or carnauba wax. By choosing the core material from materials listed above it is possible to embed the volatile substance in the matrix material and at the same time to provide a core being solid or semi-solid so that covering this core by the carrier material will result in a non-confluent coating layer of the carrier.

For obtaining a more stable core preferably up to 20% by weight of the at least one matrix material is replaced by at least one texturizer, selected from the group of polymers, such as proteins, preferably whey protein, corn protein, wheat protein, rape protein and pea protein, polysaccharides such as celluloses, starches and pectin; montmorillonites; stearates; sulphates and silicates, preferably precipitated silica. By incorporating the texturizer in the core it is possible to further enhance the stability of the particle as such and at the same time to further increase retainment of the volatile substance in the core material of the particle. By incorporating a texturizer in the core, higher amounts of volatile substances, up 40% by weight and more, can be achieved in the core.

For obtaining a non-confluent layer able to increase the recovery rate of the volatile substances in the core even better the invention is further developed in that the carrier material of the non-confluent layer comprises at least one hydrophobic substance. By adding at least one hydrophobic substance that is preferably semi-solid or liquid at the mixing temperature of the hydrophobic substance and the carrier material to the carrier material one can obtain a material for the non-confluent layer which is still powdery and resembles to the material of the core without being identical to the same. Preferably the at least one hydrophobic substance is therefore selected from an essential oil or a plant extract both being preferentially prepared from a plant selected from the group of oregano, thyme or mint, peppermint, or from an ingredient, component or compound of the essential oil or plant extract, which also may be derived from synthetic or biotechnological production, preferably selected from the group of monoterpenes, preferably α-terpinene, linalool, geraniol, menthol, citronellal, carvone, menthone, sesquiterpenes preferably farnesol, farnesene, α-bisabolol and α-caryophyllene; and aromatic compounds preferably carvacrol, thymol, cinnamaldehyde, anethole and eugenol. By adding hydrophobic substances to the carrier it is possible to incorporate higher amounts of volatile substances like essential oils into the whole particle and especially into the non-confluent layer whereby particles having an excess amount of volatile substance can be obtained. In many applications such as food or feed additive the amount of flavourings will be essential for obtaining a functional and tasty product and therefore it might be helpful having a non-confluent layer containing also flavourings.

Surprisingly it was found that the adherence of the non-confluent layer to the core will not be adversely affected if the carrier of the non-confluent layer contains at least 100% by weight, preferably at least 150% by weight, more preferably at least 220% by weight and most preferably at least 400% by weight of the hydrophobic substance based on the mass of the carrier material without the at least one hydrophobic substance. The effect achieved is that the total amount of hydrophobic substances in the particle augments which leads to a product having for example an higher content of flavourings, which help for example to mask ill-tasting substances being contained in the core or also in the product whereto the particles are added.

For obtaining a longer duration of storage of the particles it is possible according to the present invention to surround the particle by at least one confluent layer. Such a confluent layer may have a thickness of not more than 100 μm, preferably not more than 50 μm, more preferably not more than 20 μm and most preferably not more than 10 μm, whereby particles are obtained which are sufficiently small for being used in many applications such as in medicine, feed or food applications as flavouring or also as substances with antibacterial efficacy in cleaning and washing formulations based on a liquid and/or dry solution. Furthermore the confluent layer may comprise at least one coating material and optionally at least one active ingredient or also a coating material and a flavouring agent.

Such a confluent layer may consist of each material being convenient and is preferably a hydrophobic layer in which the coating material is preferably selected from the group of hydrogenated vegetal triglycerides, preferably palm oil, sunflower oil, corn oil, rapeseed oil, peanut oil and soybean oil; waxes, preferably candelilla wax and carnauba wax; essential oils, preferably monoterpenes, preferably limonene, α-terpinene, linalool, geraniol, menthol, citronellal, carvone and menthone, sesquiterpenes, preferably farnesol, farnesene, α-bisabolol and α-caryophyllene; and aromatic compounds preferably carvacrol, thymol, cinnamaldehyde, anethole and eugenol. Thereby it is possible to obtain particles having a hydrophobic surface which can preferably be used in hydrophobic environments. A hydrophobic coating, for example, may confer a degree of resistance to dissolving in an aqueous environment and would result in a product that would be protected through passage of the upper gastrointestinal tract such as the stomach of monogastric animals or the rumen of ruminant animals.

In the same manner it is possible to prepare particles having a coating consisting of a hydrophilic confluent layer in which the coating material is preferably selected from the group of biopolymers, preferably carbohydrates like starch or cyclodextrin, and polyethylene glycol; hydrocolloids, preferably carrageenan, alginates and gum arabicum; wheat gluten; salts preferably chlorides, nitrates, phosphates and sulphates, more preferably sodium sulphate and ammonium sulphate. These particles may be used in an especially hydrophilic environment and show a long storage time. A hydrophilic coating may confer resistance to steam conditioning and pelleting when such particles are incorporated in animal feed.

The invention aims also to a process for preparing a particle containing at least a volatile substance comprising the steps of:

(i) forming a melt of an at least one matrix material, whereas the matrix material is selected from the group of fats, hydrogenated triglycerides and waxes that are solid or semi-solid at 20° C. and 1 atmosphere, whereas the at least one volatile substance has a vapor pressure at 125° C. of between 10 mmHg and 200 mm Hg, (ii) forming a melt-mixture comprising an emulsion, dispersion, solution or suspension of the at least one volatile substance in the melt, by incorporating it into the melt, (iii) forming discrete cores of the melt mixture, whereby the cores contain 30% by weight to 97% by weight of matrix material based on the total mass of the core, (iv) cooling the discrete cores, (v) mixing the cores with at least one carrier material optionally containing at least one hydrophobic substance thereby forming a first non-confluent layer, whereas the carrier material is an inorganic material having a porous structure and a D50 of 1 to 300 µm, whereas the core has an average surface coverage by the non-confluent layer of 1% to 50%, (vi) optionally surrounding the particle with at least one confluent layer and/or further non-confluent layer(s), whereby the presence of the first non-confluent layer increases the recovery of the volatile substance in the core during the granulation of fluidization.

With such a process it is possible to obtain very small particles containing in its core at least one volatile substance. Evaporation of this volatile substance from the core is prevented by attaching to the surface of the core a non-confluent layer comprising at least one matrix material. The process steps for obtaining this particle are very simple and no expensive and complicated devices are necessary for the preparation of the particle. Notwithstanding it is possible to obtain with this process a particle which shows the advantages described above.

Especially good results can be obtained if the core is obtained by matrix encapsulation techniques preferably by spray cooling. Applicable spray cooling techniques are described in detail in Gouin, S. (2004) Microencapsulation: industrial appraisal of existing technologies and trends. Trends Food Sci. Technol. 15, 330-347 and WO 99/61145 Method and apparatus for forming an encapsulated product matrix. By using such a technique it is possible to prepare cores containing up to 50% by weight of a volatile substance and the cores obtained can be further processed, especially coated with the non-confluent layer without any significant change in its temperature.

For achieving a non-confluent layer covering not more than 50%, especially not more than 25% and preferably not more than 15% of the surface of the core the process can be conducted in such a manner that the core material is mixed by shaking, slow stirring or circulating in a batch container at a temperature of 20° C.±5° C. with the carrier material. With such a process it is possible to form liquid bridges between the volatile substance being contained in the core and the carrier material being contained in the non-confluent layer. Although no chemical bonding exists between core and non-confluent layer the non-confluent layer cannot easily separate from the core after having it formed thereon. The present process is therefore cheap and at the same time very efficient for the preparation of the particle according to the present invention.

For obtaining a further protection of the core containing and/or comprising a volatile substance a confluent layer is applied by a suitable coating technology, preferably fluidized bed coating to the particle containing the core and the non-confluent layer. Applicable fluidized bed coating techniques are described in detail in Nienow, A. W. (1995) Fluidised bed granulation and coating: applications to materials, agriculture and biotechnology. Chem. Eng. Comm. 139, 233-253 or WO 03/033125 "Process for the production or coating of granules, apparatus for carrying out the process, and granules obtainable thereby".

It must be noted that as used herein, the singular forms "a", "an" and "the" include plural references and vice versa unless the context clearly indicates otherwise. Thus, for example, a reference to "a particle" or "a process" includes one or more of such particles or processes, respectively, and a reference to "the process" includes equivalent steps and processes that could be modified or substituted known to those of ordinary skill in the art. Similarly, for example, a reference to "parties", "processes" or "volatile substances" include "a particle", "a processes" or "a volatile substance", respectively.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term". For example, A, B and/or C means A, B, C, A+B, A+C, B+C and A+B+C.

The term "about" or "approximately" as used herein means within 20%, preferably within 10%, and more preferably within 5% of a given value or range. It includes also the concrete number, e.g., about 20 includes 20.

The term "more than" includes the concrete number. For example, more than 20 means≥20.

Throughout this specification and the claims or items, unless the context requires otherwise, the word "comprise" and variations such as "comprises" and "comprising" will be understood to imply the inclusion of a stated integer (or step) or group of integers (or steps). It does not exclude any other integer (or step) or group of integers (or steps). When used herein, the term "comprising" can be substituted with "containing", "composed of", "including", "having" or "carrying." When used herein, "consisting of" excludes any integer or step not specified in the claim/item. In each instance herein any of the terms "comprising", "consisting essentially of" and "consisting of" may be replaced with either of the other two terms.

It should be understood that this invention is not limited to the particular methodology, protocols, material, reagents, and substances, etc., described herein. The terminologies used herein are for the purpose of describing particular embodiments only and are not intended to limit the scope of the present invention, which is defined solely by the claims/items.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

DESCRIPTION OF THE DRAWINGS

For further clarifying the particles as well as the process for obtaining the same the invention is described in the following by means of figures and examples.

Therein:

FIG. 1 consisting of FIG. 1A and FIG. 1B, wherein

FIG. 2 consisting of FIG. 2A and FIG. 2B, wherein

FIG. 2A shows the cross section through a particle obtained by example 1a. The diameter of the core and the length of selected carrier material particles are drawn in.

FIG. 2B shows the cross section through a particle obtained by example 1 b. The diameter of the core and the length of selected carrier material particles are drawn in.

DETAILED DESCRIPTION OF THE INVENTION

Example 1

Figure 1A:
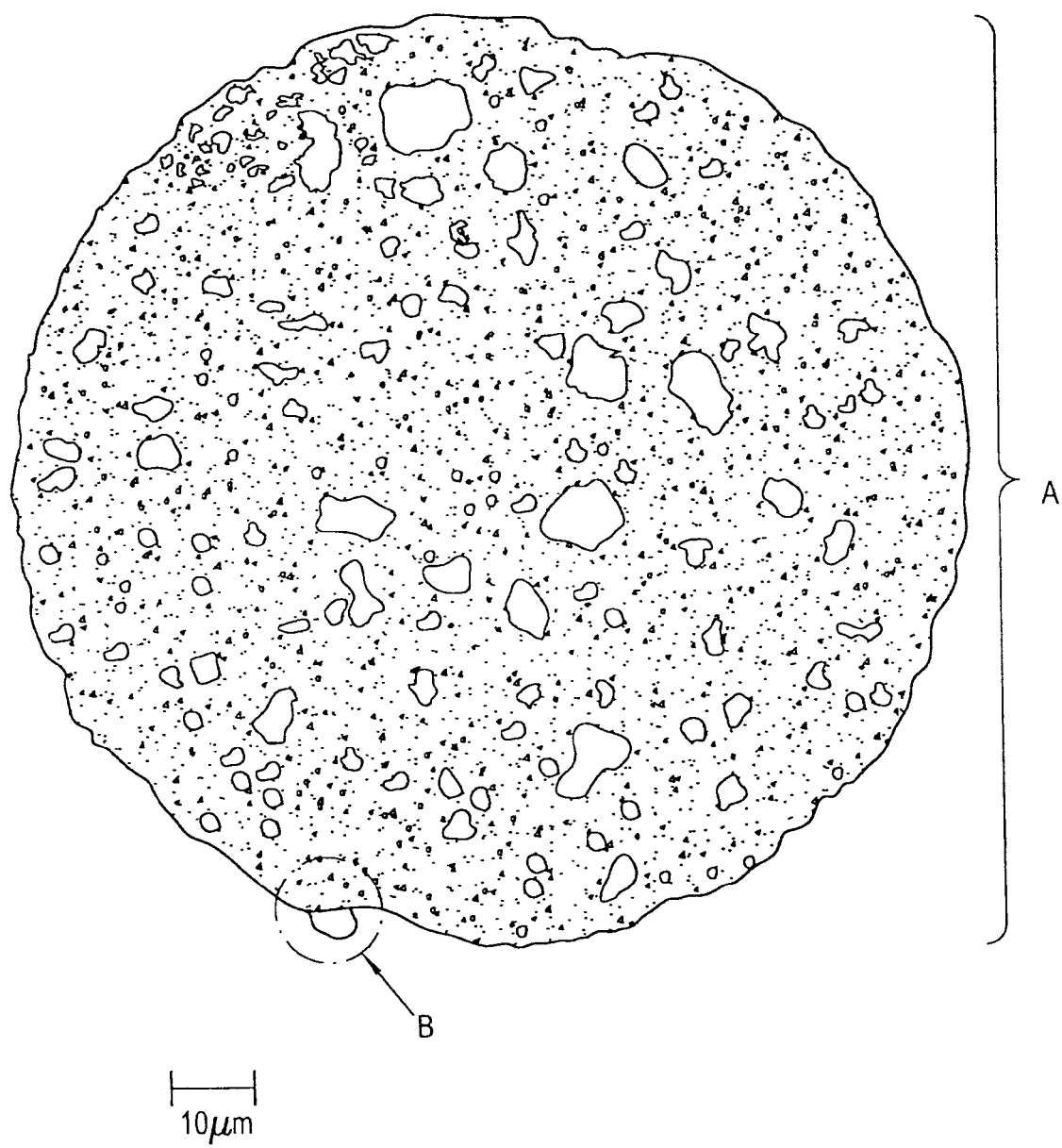
FIG. 1A shows the cross section through a particle obtained by example 1a having a core (A) and a non-confluent layer (B).

In example 1a-c) the production of particles consisting of a core comprising a volatile substance and a non-confluent layer is described on a laboratory scale.

Example 1a

1) Generation of the Core
i) Generation of a Melt of a Matrix Material

Hydrogenated sunflower oil (HSO) (CAS-No: 69002-71-1; ADM Sio; VGB5ST; MP: 33-70° C.; White flakes at 20° C.) was molten in a stainless steel vessel at a melting temperature of 85° C. 600 g of the HSO were poured into a 2 L glass bottle. The glass bottle was placed onto a magnetic stirrer and the temperature was kept at 85° C. Under stirring 100 g of a texturizer (hydrophobic precipitated silicate; Sipernat®D17; CAS-No: 68611-44-9; $D_{50}$=10 μm) were mixed to the molten HSO.

ii) Incorporation of a Volatile Substance into the Melt

As soon as the hydrophobic precipitated silicate was completely dissolved 300 g of a mixture of volatile substances (1) consisting of 44% by weight synthetic carvacrol (CAS-No: 499-75-2), 47% by weight caraway oil (CAS-No: 8000-42-8) and 9% by weight oregano oil (CAS-No: 862374-92-3) were added. This addition reduced the temperature of the melt to approx. 60° C. The final melt thus contains 60% by weight hydrogenated sunflower oil (CAS-No: 69002-71-1), 10% by weight texturizer (CAS-No: 68611-44-9) and 30% by weight volatile substances.

iii) Formation of Discrete Cores from the Melt Mixture

The mixture was re-heated to 80° C. and pumped through a hose to the spraying fluid connection of a spinning disc (fluid stream: 5.7 l/h). The spraying fluid is defined as the melt mixture forming the core. The spinning disc is a horizontally oriented disc with fine grooves on the surface. Liquid material (e.g. the melt) flowing over the surface of the rotating spinning disc forms fine droplets when leaving its edges. The rotation of the spinning disc (3275 rpm) forced the material mixture to leave the disc in form of fine droplets. The spinning disc is assembled within a prilling tower, which is a room (L×B×H; 90×70×200 cm) in which the spinning disc is installed.

iv) Cooling of the Discrete Cores

Cooling was achieved by keeping the prilling tower at max. 30° C., a temperature at which the melt droplets hardens automatically. When the droplets reached the prilling tower bottom the droplets had hardened and a powder had formed ($D_{50}$=approx. 200 μm). In the following this powder is named core.

2) Generation of the Non-Confluent Layer

Precipitated silicate (Sipernat®22S; CAS-No: 112926-00-8; $D_{50}$=13.5 μm; spec. surface=190 m²/g) was used as the carrier material for the non-confluent layer.

3) Application of the Non-Confluent Layer onto the Core

The product from step 1) (1000 g) was filled into the mixing chamber of a mixing device (kitchen aid). Under stirring at lowest level (40 rpm) 37.5 g of the carrier material from step 2) were admixed to the core until all visible lumps were divided and the material mixture was homogenized.

Example 1b

1) Generation of the Core: See Step 1) from Example 1a
2) Generation of the Non-Confluent Layer 37.5 g precipitated silicate (Sipernat®22S; CAS-No: 112926-00-8; $D_{50}$=13.5 μm; spec. surface=190 m²/g) were weighed into the mixing chamber of a kitchen aid. Under stirring 75 g of a hydrophobic substance, being mint oil (CAS-No: 90063-97-1) was pipetted onto the silicate. The materials were mixed with the mixing device at 40 rpm kitchen aid at the lowest level until no humid lumps or free hydrophobic substance were visible any more. In the following, the precipitated silicate that contains at least one hydrophobic substance, e.g. an essential oil is named: loaded non-confluent layer.

3) Application of the loaded non-confluent layer onto the core

The product from step 1) (1000 g) was filled into the mixing chamber of the kitchen aid. Under stirring at lowest level the loaded non-confluent layer from step 2)

(112.5 g) was admixed to the core until all visible lumps were divided and the material mixture was homogenized.

Example 1c

1) Generation of the Core: See Step 1) from Example 1a
2) Generation of the Non-Confluent Layer
   37.5 g precipitated silicate (Sipernat®22S; CAS-No: 112926-00-8; $D_{50}$=13.5 µm; spec. surface=190 m$^2$/g) were weighed into the mixing chamber of a kitchen aid. 37.5 g of a hydrophobic substance, being crystalline menthol (CAS-No: 2216-51-5) were weighed into a beaker glass and molten at moderate temperature (40-45° C.). The opening of the beaker glass was covered with aluminium foil to avoid menthol evaporation. Under stirring at the lowest level the molten menthol was poured over and mixed with the precipitated silicate until no humid lumps or free menthol was visible any more.
3) Application of the Loaded Non-Confluent Layer onto the Core
   The product from step 1) (1000 g) was filled into the mixing chamber of the kitchen aid. Under stirring at lowest level the loaded non-confluent layer from step 2) (75 g) was admixed to the core until all visible lumps were divided and the material mixture was homogenized.

Figure 1B:
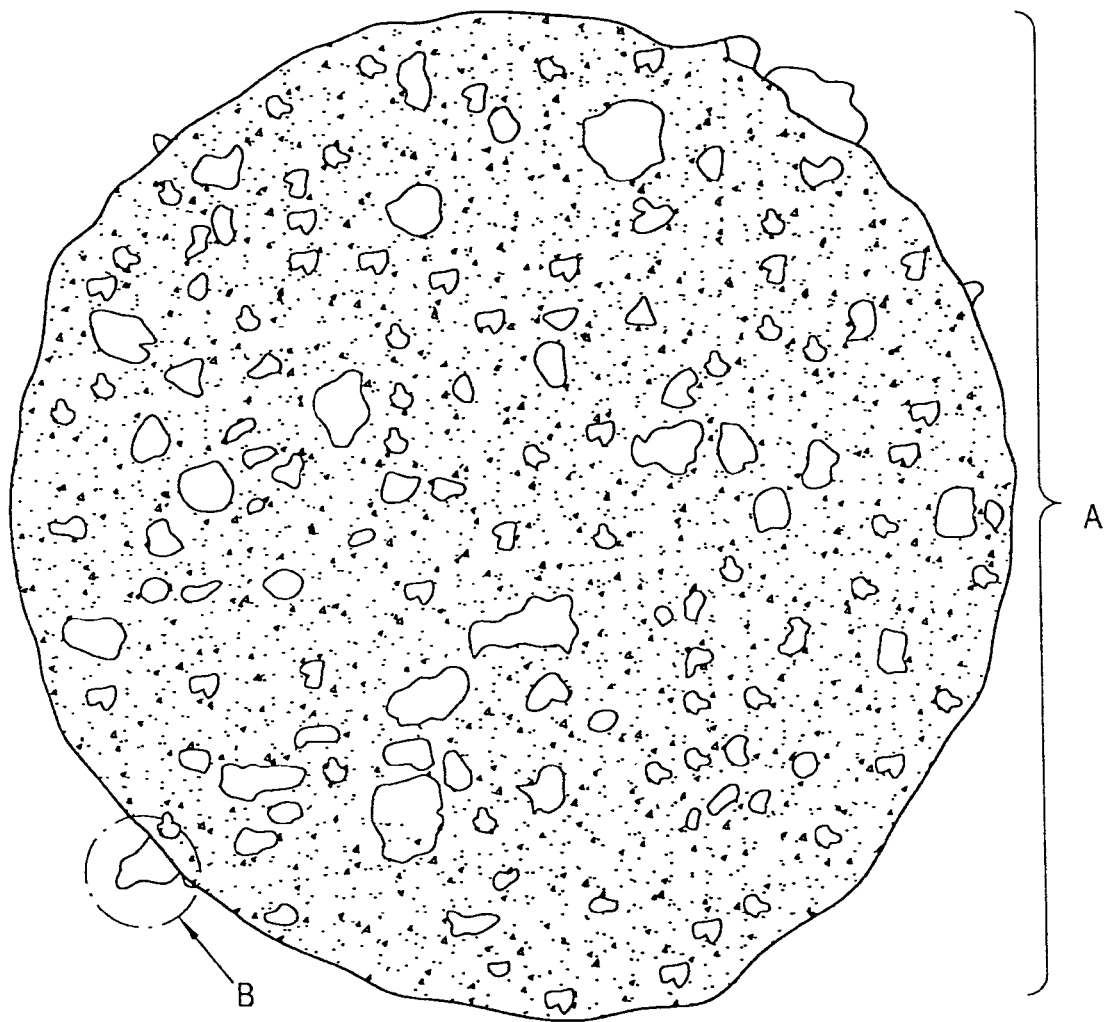
FIG. 1B shows the cross section through a particle obtained by example 1 b having a core (A) and a non-confluent layer (B).

In addition to step 3) example 1a-c were investigated via scanning electron microscopy (SEM) to see whether the structure of a core surrounded by a non-confluent layer is feasible (FIGS. 1A and 1B).

Alternatively, to the mixture of volatile substances (1) described in example 1a the following mixtures of volatile substances can exemplary also be used within the scope of the invention:
(2): 30% by weight orange essential oil; 70% anise essential oil
(3): 13% by weight oregano oil; 58% by weight thyme oil; 29% by weight caraway oil
(4): 51% by weight peppermint oil; 10% by weight majoram oil; 16% by weight clove oil; 23% by weight star anise oil
(5): 67% by weight mint oil; 2% wintergreen oil; 22% by weight L-carvone; 9% by weight methyl salicylate
(6): 100% by weight oregano oil
(7): 45% by weight cinnamon bark oil; 9% by weight trans-cinnamaldehyde; 18% by weight clove oil; 6% by weight eugenol; 2% by weight β-caryophyllene; 20% by weight by orange oil
(8): 17% by weight carvacrol; 78% by weight thymol; 5% by weight D-carvone
(9): 17% by weight of garlic oil; 80% by weight of fennel oil; 3% by weight trans-anethole
(10): 41% by weight peppermint oil; 34% by weight clove oil; 25% by weight thymol
(11): 100% by weight carvacrol Example 2

The structure of the particles comprising a core and a non-confluent layer were investigated via SEM. Therefore, the particles were spread over a plastic foil (thickness approx. 0.5 mm) and poured with a molten epoxy resin. When the resin had hardened the plastic foil covered with the particles and the resin was fixed with a clamp and put into the centre of a whole cylinder (d=approx. 2.5 cm, h=approx. 1 cm). The cylinder was completely filled with molten epoxy resin again. As soon as the resin had hardened, it was loosen from the cylinder and fixed into a grinding machine. The sample was ground until a level was reached that the particles were sliced. The cross section through the single particles was analyzed via SEM (Zeiss; Supra 35; Smart SEM V05.04). This revealed that all particles described in example 1 have a non-confluent layer at the surface of the core as exemplary shown in FIGS. 1A and 1B.

Example 3

On basis of the analysis described in example 2 the average surface coverage of the cores by the non-confluent layer could be calculated. Therefore 10 to 20 particles of each sample/batch were analyzed. The circumference of each core was calculated by measuring its diameter and applying the formula U=π*d, with U is the circumference, π is Pi and d is the diameter of the core. The length of all carrier material particles of the non-confluent layer ($l_{1,2,3\ldots,n}$) that are attached to the core were measured (see FIGS. 2A and 2B). The length of the carrier material particles is defined as the length of the contact line between the carrier material particles and the core. The surface coverage in percentage of one core (the core coverage CC) by the non-confluent layer was calculated according to the formula:

$$CC_{1,2,3,\ldots,n} = \frac{\text{SUM}(l1, 2, 3, \ldots, n)}{U} * 100$$

Figure 2A:
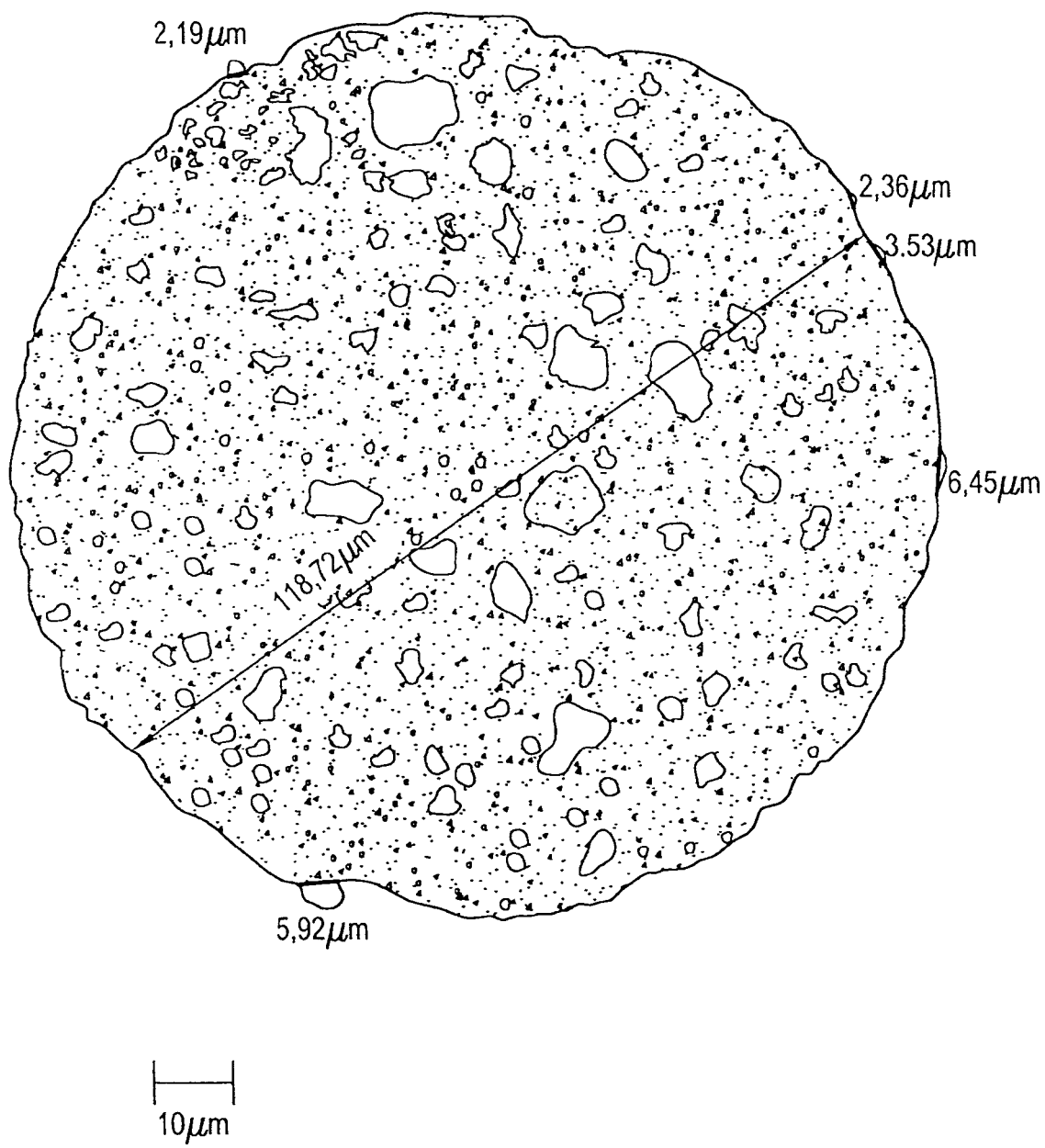
Figure 2B:
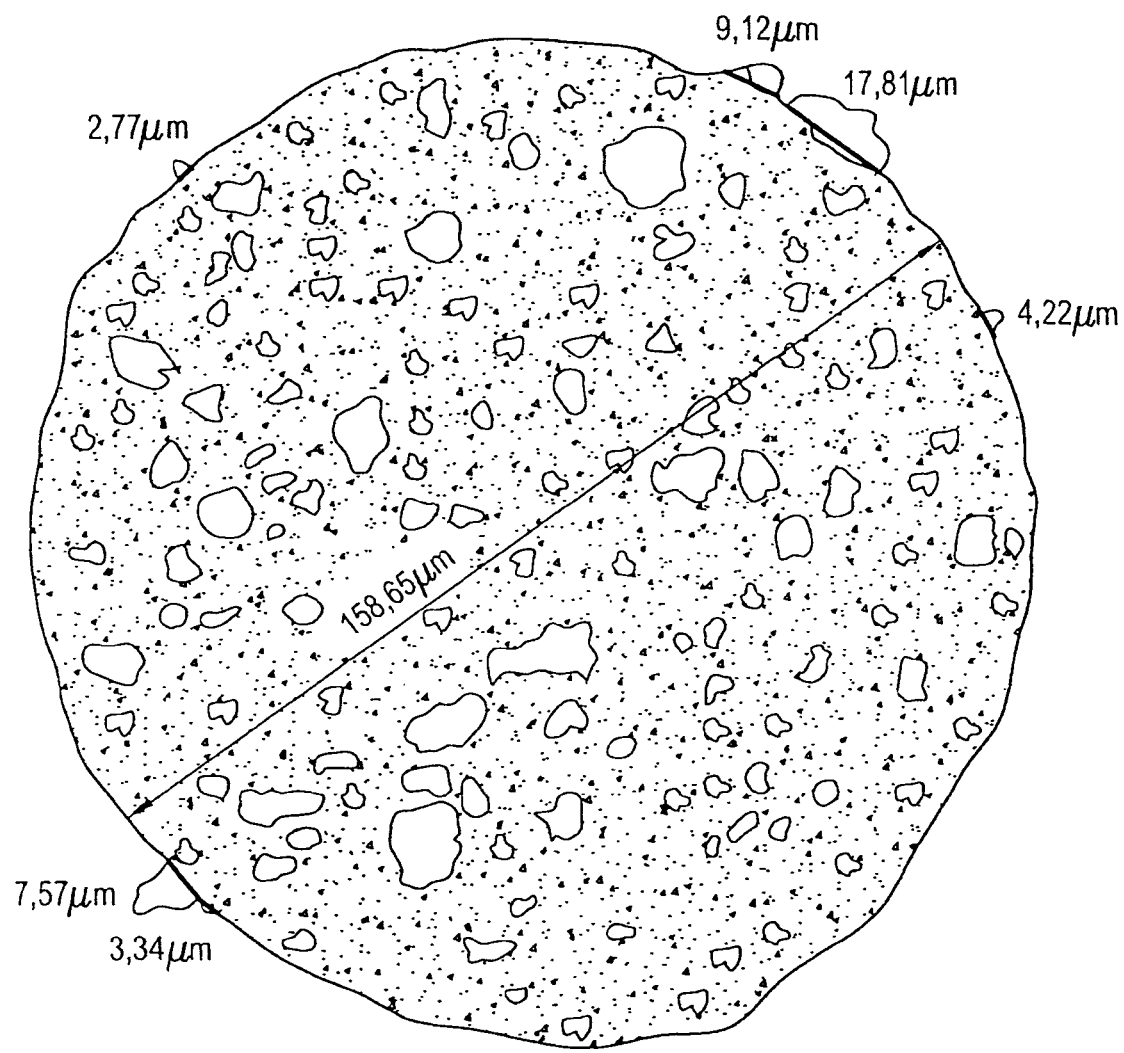

The average surface coverage of the cores by the non-confluent layer was determined by measuring the CC of 10 to 20 particles of one sample and by calculating the average. Exemplarily, the calculation of the core coverage for the particle shown in FIG. 2A is shown:

$$d_1 = 118.72 \text{ µm and } l_i = 2.19 \text{ µm}, l_2 = 3.53 \text{ µm},$$
$$l_3 = 2.36 \text{ µm}, l_4 = 6.45 \text{ µm and } l_5 = 5.92 \text{ µm}.$$
$$U = \pi * d; U = \pi * 118.72 \text{ µm} = 372.97 \text{ µm}$$
$$\text{SUM}(l_{1,2,3,4,5}) =$$
$$2.19 \text{ µm} + 3.53 \text{ µm} + 2.36 \text{ µm} + 6.45 \text{ µm} + 5.92 \text{ µm} = 20.45 \text{ µm}$$
$$CC_1 = \frac{\text{SUM}(l_{1,2,3,\ldots,n})}{U} * 100 = \frac{20.45 \text{ µm}}{327.97 \text{ µm}} * 100 = 5.48\%.$$

Example 4

Cores were prepared as described in example 1a (in batches 5-7 the weight percentages have been changed according to table 1. The non-confluent layer for batch 1, 5 and 6 was applied as described in example 1a and all other batches as described in example 1b, however in amounts as indicated in table 1. All batches were analyzed via SEM with the method described in example 2 and the average surface coverage of each sample was calculated following example 3. The results showed that the average core coverage of a sample increases with increasing amount of the precipitated silicate loaded with a hydrophobic substance.

TABLE 1

Composition of the particles and average core coverage of the non-confluent layer

| | Core | | | Non-confluent layer | | |
|---|---|---|---|---|---|---|
| Batch No. | Matrix material (HSO) [% wt] | Texturizer [% wt] | Volatile substance mixture (1) [% wt] | Carrier material [% wt] | Hydrophobic substance [% wt] | Core coverage Average [%] |
| 1 | 57.83 | 9.64 | 28.91 | 3.62 | — | 9.9 |
| 2 | 61.55 | 4.73 | 28.40 | 1.77 | 3.55 | 5.9 |
| 3 | 52.13 | 10.79 | 26.97 | 3.37 | 6.74 | 9.8 |
| 4 | 53.07 | 4.08 | 24.49 | 6.12 | 12.24 | 10.4 |
| 5 | 95.29 | — | 2.94 | 1.77 | — | 1.3 |
| 6 | 32.86 | 14.08 | 46.94 | 6.12 | — | 23.7 |
| 7 | 44.90 | 4.08 | 32.66 | 6.12 | 12.24 | 20.8 |

Example 5

The particles from example 4 comprising were fluidized for 20 minutes. Therefore 150 g of each batch were put into the process chamber of a laboratory scale fluidized bed plant (DMR, WFP-Mini) and the material was fluidized with a process air temperature of 27° C. and an air stream of 10-15 m³/h (depending on the fluidization of the cores) and a product temperature of about 28° C. As negative controls cores with the identical core composition but without the non-confluent protection layer were fluidized under the same conditions. Thus 1 control was required for batches 1-4 and 1 control for each of the batches 5-7. Recovery rates of four volatile compounds present in the volatile substance mixture (1) were analyzed (see table 2).

After 20 minutes fluidization a sample of a few grams was taken and the material was analyzed for its residual volatile substance content via gas chromatography (GC). Therefore 0.10 to 0.11 g of the fluidized particles were weighed into a 2 mL plastic tube. The exact sample weight was determined using an analytical balance (accuracy 0.0001 g) and noted. 1.5 mL ethyl acetate (EtOAc) were added to the particles and the plastic tubes were closed. The material was shaken for 10 minutes and afterwards centrifuged for ten minutes at 12500 rpm. The supernatant was collected in a 15 mL plastic tube. To release all the volatile material from the particles this extraction step with EtOAc was performed three times and the supernatants were collected together in the same plastic tube. Additionally 100 μL of the internal standard (Dicyclohexylmethanol, CAS-No: 4453-82-1, approx. 0.5 g/L) were added and the plastic tube was made up to a volume of 5 mL with EtOAc.

For the quantitative measurement of the content of the volatile substances after 20 minutes fluidization the volatile substances a Shimadzu gas chromatograph equipped with a SSL-inlet and a FID detector (Shimadzu GC-2010 plus) was used. The liner was straight with glass wool on top, the inlet maintained at 250° C. Injection volume was 1 μl at a split ratio of 10. The carrier gas was helium (AlphaGaz 1, purity 99,999%) and the gas flow was 1.6 ml in constant flow mode. The separation column was a polar WAX column with length 30 m, inner diameter 0.25 mm and a film thickness of 0.25 μm (Zebron ZB-WAXplus, Phenomenex). The oven program started with 60° C. for 1 min and ramped with 5° C./min to 90° C., 7° C./min to 200° C., 30° C./min to 260° C. which was then kept for 7 min. The FID detector sampling rate was of 20 Hz, hydrogen flow was 40 ml/min, zero air flow 400 ml/min and makeup gas (He) flow was 30 ml/min and it was maintained at 280° C. Therefore 1 mL of the solution described above were filled into a GC vial. The vial was closed using the respective screw lid and put into the auto sampler tray. The analysis were started using the Labsolution software. The data analysis was performed with the MassHunter Quantitative Analysis program.

The volatile substance content of each product after 20 minutes fluidization ($VSC_{20min}$) was compared with the volatile substance content of the original sample ($VSC_{orig.}$) that has not been fluidized. The recovery was calculated by the following formula:

$$\text{Recovery [\%]} = \frac{VSC_{20min}}{VSC_{orig.}} * 100$$

e.g. for if:

$VSC_{orig.}$=8.3 mg/g and $VSC_{20min}$=8.0 mg/g

The recovery is:

$$\text{Recovery} = \frac{VSC_{20min}}{VSC_{orig.}} * 100 = \frac{8.0 \frac{mg}{g}}{8.3 \frac{mg}{g}} * 100 = 96\%$$

TABLE 2

Volatile substance recovery after 20 minutes [%]

| Batch No. | Linalool | Carvone | Thymol | Carvacrol |
|---|---|---|---|---|
| 1-4 - Control | 75 | 82 | 81 | 83 |
| 1 | 97 | 100 | 100 | 100 |
| 2 | 100 | 100 | 100 | 100 |
| 3 | 100 | 96 | 100 | 100 |
| 4 | 95 | 91 | 89 | 94 |
| 5 - Control | 74 | 75 | 77 | 79 |
| 5 | 95 | 90 | 95 | 94 |
| 6 - Control | 73 | 77 | 80 | 79 |
| 6 | 99 | 96 | 100 | 99 |
| 7 - Control | 71 | 80 | 78 | 79 |
| 7 | 97 | 98 | 100 | 100 |

Example 6

Five batches of particles consisting of a core comprising a volatile substance and a non-confluent layer were produced. All cores were produced following example 1a, however the amount of texturizer and HSO was adapted according to table 3.

TABLE 3

Composition of the core

| Batch No. | Volatile substance in core [% wt] | Matrix material (HSO) [% wt] | Texturizer [% wt] |
|---|---|---|---|
| 1 | 30 | 58 | 12 |
| 2 | 30 | 65 | 5 |
| 3 | 30 | 68 | 2 |
| 4 | 30 | 69 | 1 |
| 5 | 30 | 70 | — |

The cores were furnished with a non-confluent layer following example 1b. All batches were fluidized for 20 minutes under the same conditions as described in example 5 and the recovery rates of the volatile substance in the core were determined via GC as described in example 5. In parallel cores with the same compositions as shown in table 3 without the non-confluent layer protecting the volatile substances in the core were fluidized and used as negative control batches. Table 4 shows the recoveries of single compounds of the volatile substances.

TABLE 4

| | Volatile substance recovery [%] | | | |
|---|---|---|---|---|
| Batch No. | Linalool | Carvone | Thymol | Carvacrol |
| 1 - Control | 70 | 69 | 78 | 81 |
| 1 | 100 | 100 | 98 | 100 |
| 2 - Control | 72 | 78 | 72 | 82 |
| 2 | 100 | 100 | 100 | 100 |
| 3 - Control | 71 | 78 | 77 | 85 |
| 3 | 100 | 100 | 100 | 100 |
| 4 - Control | 78 | 75 | 79 | 84 |
| 4 | 100 | 100 | 100 | 100 |
| 5 - Control | 77 | 78 | 82 | 87 |
| 5 | 92 | 98 | 100 | 95 |

Example 7

Particles consisting of a core and a non-confluent layer were produced. All cores were produced following example 1a, however with different matrix materials (see batch 2-3 of table 5). To evaluate whether the protective effect of the non-confluent layer is influenced by the type of the matrix material hydrogenated rapeseed oil (CAS-No: 84681-71-0, ADM Sio; VGB6; MP: 68-74° C.; White flakes at 20° C.) and hydrogenated soybean oil (CAS-No: 8016-70-4, ADM Sio; VGB4; MP: 68-71° C.; White flakes at 20° C.) have been used.

TABLE 5

| | Composition of the core in % wt | | |
|---|---|---|---|
| Batch No. | Volatile substance | Matrix material | Texturizer |
| 1 | 30 | 60<br>Hydrogenated sunflower oil (HSO) | 10 |
| 2 | 30 | 60<br>Hydrogenated rapeseed oil | 10 |
| 3 | 30 | 60<br>Hydrogenated soybean oil | 10 |

The cores were furnished with a non-confluent layer following the performance described in example 1b. All batches were fluidized under the same conditions as described in example 5 and the recovery of the volatile core substance was determined via GC as described in example 5. Table 6 shows the recovery of selected single compounds of the volatile substance mixture.

TABLE 6

| | Volatile substance recovery [%] | | | |
|---|---|---|---|---|
| Batch No. | Linalool | Carvone | Thymol | Carvacrol |
| 1 | 100 | 96 | 100 | 100 |
| 2 | 91 | 98 | 100 | 98 |
| 3 | 88 | 98 | 96 | 94 |

Example 8—Core Composition

Four batches of particles consisting of a core comprising a volatile substance and a non-confluent layer were produced. All cores were produced following example 1b and furnished with a non-confluent layer following the performance described in example 1b. To see whether the concentration of the core substance has an influence on the inventive protective effect, for each batch another concentration of the volatile core substance was used. The compositions of the different cores are listed in table 7.

TABLE 7

| | Composition of the core in % wt | | |
|---|---|---|---|
| Batch No. | Volatile substance in core [% wt] | Matrix material (HSO) [% wt] | Texturizer [% wt] |
| 1 | 5 | 85 | 10 |
| 2 | 10 | 80 | 10 |
| 3 | 20 | 70 | 10 |
| 4 | 40 | 50 | 10 |

All four batches were fluidized for 20 minutes under the same conditions as described in example 5 and the recovery of the volatile core substance was determined via GC as described in example 5. Table 8 shows the recovery of selected single compounds of the volatile substance mixture. The protective effect of the non-confluent layer increases with increased volatile substance concentration in the core.

TABLE 8

| | Volatile substance recovery [%] | | | |
|---|---|---|---|---|
| Batch No. | Linalool | Carvone | Thymol | Carvacrol |
| 1 - Control | 65 | 71 | 83 | 88 |
| 1 | 92 | 88 | 100 | 98 |
| 2 - Control | 68 | 75 | 81 | 85 |
| 2 | 95 | 89 | 100 | 100 |
| 3 - Control | 61 | 69 | 80 | 82 |
| 3 | 100 | 100 | 100 | 100 |
| 4 - Control | 69 | 74 | 78 | 87 |
| 4 | 100 | 100 | 100 | 100 |

Example 9—Volatility of Volatile Core Substances

Cores and non-confluent layers thereto were prepared as describes for batches 1-4 and control 1-4 in examples 4. All batches were fluidized for 20 minutes under the same conditions as described in example 5 and the recovery of the volatile core substance was determined via GC as described in example 5.

The recoveries of 13 selected compounds with vapor pressures between 11.3 mm Hg and 185.8 mm Hg at 125° C. were analyzed and listed in table 9.

The comparison of control to batch 1 shows that the application of the (non-loaded) carrier as non-confluent layer already has a protective effect on the volatile substances present in the core. The batches 2-4 reveal that the loaded carrier material has an even better protection towards the volatile substance embedded in the core.

TABLE 9

| | Volatile substance recovery [%] | | | | |
|---|---|---|---|---|---|
| | Volatile substance recovery after 20 minutes fluidization [%] | | | | Calculated vapor |
| | Control | Batch 1 | Batch 2 | Batch 3 | Batch 4 | pressure [mm Hg @ 125° C.] |
| D-Limonene | 5 | 11 | 16 | 16 | 24 | 185.8028 |
| γ-Terpinene | 0 | 6 | 9 | 12 | 17 | 156.6294 |
| p-Cymene | 1 | 6 | 12 | 12 | 23 | 170.1698 |
| Camphor | 66 | 83 | 89 | 97 | 90 | 67.8680 |
| Linalool | 52 | 88 | 87 | 100 | 88 | $^a$73.1145 |
| Terpinen-4-ol | 61 | 78 | 87 | 98 | 98 | |
| α-Terpineol | 55 | 88 | 89 | 100 | 96 | 36.7883 |
| β-Caryophyllene | 55 | 74 | 93 | 96 | 87 | |
| D-Carvone | 66 | 80 | 85 | 100 | 94 | $^a$29.0791 |
| α-Caryophyllene | 50 | 71 | 76 | 90 | 90 | |
| Eugenol | 81 | 87 | 99 | 99 | 98 | 11.2903 |
| Thymol | 81 | 89 | 98 | 98 | 93 | 19.2101 |
| Carvacrol | 99 | 98 | 100 | 100 | 100 | 16.2002 |

The vapor pressures were calculated using the Antoine equation, which describe the relation between the vapor pressure and temperature for pure compounds.

Antoine Equation:

$$\log_{10} p = A - \frac{B}{C+T}$$

Where:
p—vapor pressure of the component, mmHg
T—temperature, ° C.
A, B, C—component specific Antoine constants.
e.g.: Calculation of the vapor pressure of D-limonene at 125° C. with $$A = 7.06744, B = 1691.1486, C = 227.441$$
$$\log_{10} p = 7.06744 - \frac{1691.1486}{227.441 + 125}$$
$$\log_{10} p = 2.269052185$$
$$p = 10^{2.269052185} = 185.8028$$

The Antoine constants can be obtained from different literature sources. It is preferred to obtain them from Yaws, C. L. & Satyro, M. A., Chapter 1—Vapor Pressure—Organic Compounds, in The Yaws Handbook of Vapor Pressure (Second Edition) Antoine Coefficients, Elsevier B. V. (2015) pp 1-314. ISBN: 978-0-12-802999-2. An alternative source may be Dykyj, J., Svoboda, J., Wilhoit, R. C., Frenkel, M. & Hall, K. R., Chapter 2 Organic Compounds, C1 to C57 Part 2, in Vapor Pressure and Antoine Constants for Oxygen Containing Organic Compounds, Springer Materials (2000) pp 111-205. ISBN: 978-3-540-49810-0 (a) from which the constants have been obtained for calculating the vapor pressure from linalool and carvone (see table 9). For all other substances, the constants from Yaws & Satyro have been used.

In case different vapor pressure calculations result in contradictory results it is herein preferred that the vapor pressure of the at least one volatile substance is in the range from the vapor pressure of D-Limonene to the vapor pressure of eugenol, preferred in the range from the vapor pressure of linalool to the vapor pressure of D-carvone.

Example 10—Confluent Layer

Particles consisting of a core comprising a volatile substance and a non-confluent layer and a confluent coating layer were produced.

1) Generation of the core: See 1) from example 1a
2) Generation of the non-confluent layer: See 2) from example 1b
3) Application of the non-confluent onto the core: See 3) from example 1b
4) Surrounding the particles consisting of a core comprising a volatile substance and a non-confluent layer with a confluent layer 4a)

200 g of the particles consisting of a core comprising a volatile substance and a non-confluent layer (see example 1b, step 2)) were put into the process chamber of a laboratory scale fluidized bed plant (DMR; WFP-Mini). The particles were fluidized at an air volume stream of 10 m³/h. The inlet air temperature was slightly heated to 25° C. The product temperature was 29° C. throughout the whole process. After 5 minutes fluidization the coating process was started, therefore the spray nozzle was used in the bottom spray position (spray air pressure: 1 bar; nozzle cleaning air 0.3 bar). As confluent layer material pure hydrogenated sunflower oil (CAS-No: 68002-71-1) (70 g) was used. The confluent layer material was sucked in without controlling the spray rate.

4b)

325 g of the particles consisting of a core comprising a volatile substance and a non-confluent layer (see example 1c, step 2)) were put into the process chamber of a laboratory scale fluidized bed plant (DMR; WFP-Mini). The particles were fluidized at an air volume stream of 10 m³/h. The inlet air temperature was not heated. The product temperature was around 23° C. throughout the whole process. After 5 minutes fluidization the coating process was started, therefore the spray nozzle was used in the bottom spray position (spray air pressure: 0.5 bar; nozzle cleaning air: 0.2 bar). The confluent layer material was generated by mixing the coating material (hydrogenated sunflower oil (CAS-No: 68002-71-1, 116.82 g) with the active ingredient (crystalline menthol (CAS-No: 2216-51-5, 11.2 5 g). The confluent layer material was pumped into the system. Therefore the peristaltic pump (Watson Marlow 323) was set to the value 12. When the addition of the confluent layer material was finished the product was fluidized without being coated for further 3 minutes.

Control)

In parallel cores prepared as described in example 1a (cores without the non-confluent layer) were surrounded with a confluent layer. Therefore, 200 g of the cores were put into the process chamber of a laboratory scale fluidized bed plant (DMR; WFP-Mini). The particles could be fluidized at an air volume stream of 15 m³/h. The inlet air temperature was slightly heated to 25° C. The product temperature was 29° C. throughout the whole process. After 5 minutes fluidization the coating process was started, therefore the spray nozzle was used in the bottom spray position (spray air pressure: 1 bar; nozzle cleaning air: 0.3 bar). As confluent layer coating material pure hydrogenated sunflower oil (CAS-No: 68002-71-1) (70 g) was used. The confluent layer material was sucked in without controlling the spray rate.

GC analysis was performed as described in example 5 and revealed a recovery rate of selected volatile substances of at least 80%.

TABLE 10

| Volatile substance recovery [%] | | | | |
|---|---|---|---|---|
| Batch No. | Linalool | Carvone | Thymol | Carvacrol |
| Control | 66 | 78 | 83 | 82 |
| 4a | 82 | 91 | 92 | 100 |
| 4b | 80 | 93 | 92 | 96 |

Example 11

Cores were produced applying the same process as described in example 1a, however with a different volatile substance mixture being 10% by weight synthetic carvacrol (CAS-No: 499-75-2), 19% by weight synthetic thymol (CAS-No: 89-83-8), 68% by weight synthetic D-carvone (CAS-No: 2244-16-8) and 3.0% by weight synthetic methyl salicylate (CAS-No: 119-36-8). The calculated vapor pressure of methyl salicylate according to example 9 is 31.7730 mm Hg at 125° C.

The $D_{50}$ of the cores was 540 μm. The $D_{50}$ is defined as the particle size below which 50% of the particles of a sample are. The cores were furnished with a non-confluent layer comprising 100% by weight crystalline menthol as described in example 1c. The particles were surrounded by a confluent layer as described in example 10-4a.

As control, cores with a $D_{50}$ of 200 μm were produced. The process was the same as described in example 1a. The cores were also furnished with a non-confluent layer comprising 100% by weight crystalline menthol as described in example 1c and additionally surrounded by a confluent layer as described in example 10-4a.

The results shown in table 11 show that even with bigger cores and different essential oil mixtures imbedded in the core the maximum loss of the volatile substances in the core is 11%.

TABLE 11

| Volatile substance recovery after applying a confluent layer [%] | | | | |
|---|---|---|---|---|
| $D_{50}$ of the core [μm] | Carvone | Methyl Salicylate | Thymol | Carvacrol |
| 200 | 100 | 91 | 94 | 100 |
| 540 | 100 | 89 | 93 | 100 |

Example 12

Particles consisting of a core comprising a volatile substance and a non-confluent layer were produced following example 1b, however different carrier materials were used for the non-confluent layer. The cores were divided in various batches. Each of the batches was furnished with a non-confluent layer consisting of different carrier materials (see batches 1-8, table 12). Each carrier material was loaded with the maximum amount of the hydrophobic substance. In this case the "maximum amount" is defined as the maximum concentration of the hydrophobic substance that can be loaded onto the carrier material without moist sticky lumps being formed. The difference between various carrier materials is their medium particle size ($D_{50}$). With all carrier materials that have been tested the recovery of all volatile substance was higher than 80% (see table 13).

The absorption capacity in % by weight given in table 12 was determined visually. Therefore 20 g of each carrier material were weighed into a bowl. Under homogeneous stirring with a spoon the hydrophobic substance was added dropwise. The maximum absorption capacity was defined as the point at which the material mixture began to form moist lumps. The exact weight of the hydrophobic substance that had been added until then was noted.

All batches were fluidized for 20 minutes under the same conditions as described in example 5 and the recovery of the volatile core substance was determined via GC as described in example 5. Table 13 shows the recovery of selected single compounds of the volatile substance mixture.

TABLE 12

| Carrier materials used in batches 1-8 | | | | | | |
|---|---|---|---|---|---|---|
| Batch No. | Product name | $D_{50}$ inert carrier [μm] | Spec. surface [m²/g] | Bulk density [g/l] | SiO₂ content [wt %] | Absorption capacity [wt %] |
| 1 | Cab-O-Sil MF5 | | 192 | 30-150 | >99.9 | 391 |
| 2 | Syloid XDP 3050 | 61.4 | 320 | 275 | 99.9 | 232 |
| 3 | Perkasil GT 3000 PD | 12.9 | 164 | 70-80 | 98 | 292 |
| 4 | Zeofree 5162 | 13 | 160 | 110 | 100 | 236 |
| 5 | Hubersorb 600 | 6.7 | | | | 226 |
| 6 | Perkasil SM 660 | 19.5 | 178 | | 96.6 | 222 |
| 7 | Tixosil 38AB | 5-20 | 100-250 | | >96 | 205 |
| 8 | Tixosil 43 | 10 | | | 97.5 | 206 |

TABLE 13

| Volatile substance recovery after applying a confluent layer [%] | | | | | |
|---|---|---|---|---|---|
| Batch No. | Carvone | Thymol | Carvacrol | Linalool | Menthol |
| 1 | 96 | 97 | 97 | 90 | 94 |
| 2 | 100 | 100 | 100 | 95 | 100 |
| 3 | 100 | 100 | 100 | 94 | 99 |
| 4 | 100 | 100 | 109 | 100 | 100 |
| 5 | 95 | 86 | 100 | 82 | 91 |
| 6 | 100 | 100 | 100 | 95 | 100 |
| 7 | 98 | 100 | 100 | 93 | 96 |
| 8 | 97 | 100 | 98 | 92 | 97 |

Example 13

Figure 3:
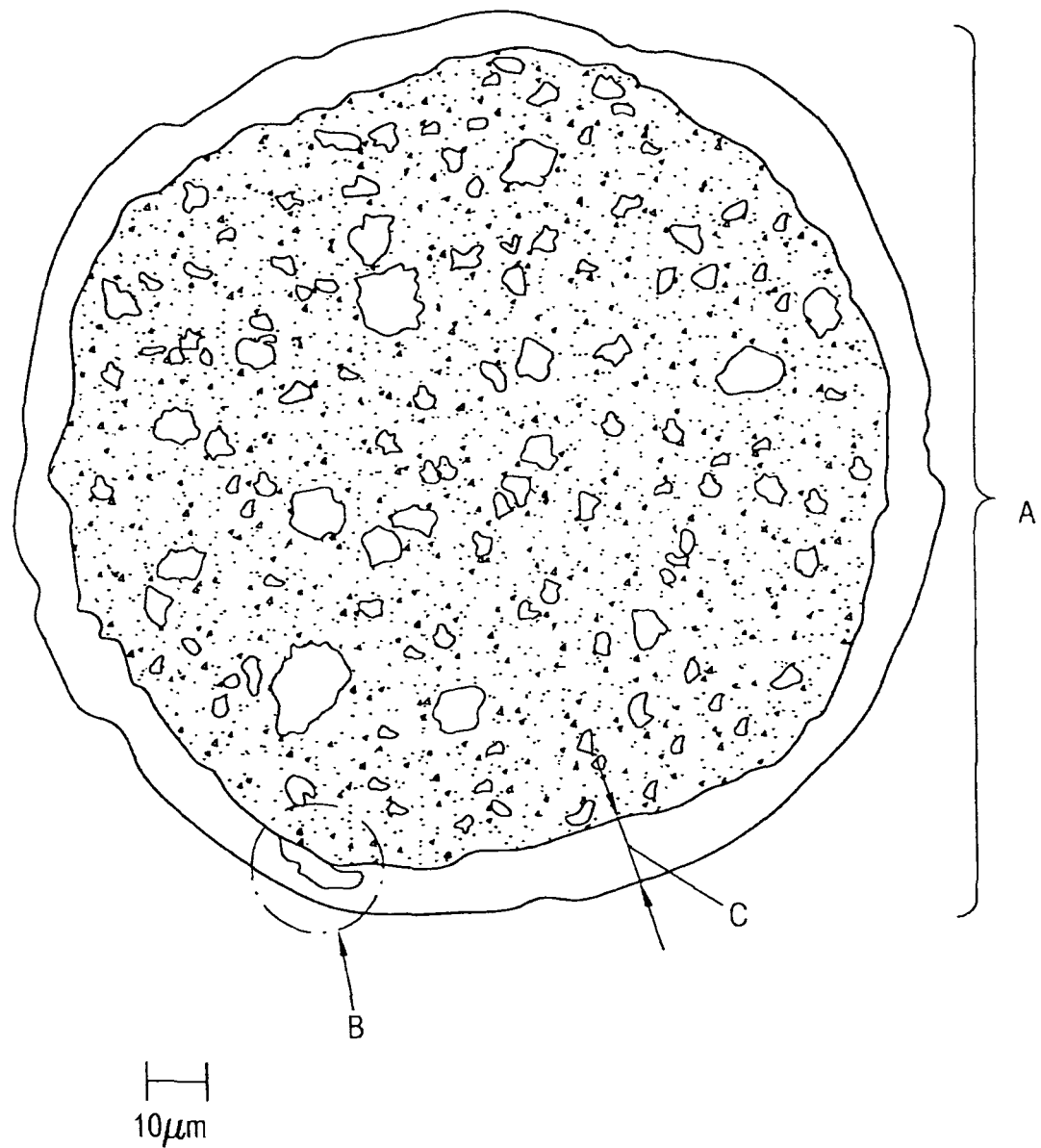
FIG. 3 shows the cross-section of a particles having a core (A) and a non-confluent layer (B) which is surrounded by a confluent layer (C)

The particles generated in example 10-4b were analyzed via SEM in the same way as described in example 2. The picture of the cross-section through one of the particles shows the three main parts of the particles, the core (A), the non-confluent coating layer attached to the surface of the core (B) and the confluent coating layer (C) (FIG. 3).

The invention claimed is:
1. A particle containing at least one volatile substance comprising:
a core comprising at least one matrix material, the at least one volatile substance, and optionally at least one texturizer;
and at least one coating layer; wherein
the at least one matrix material is selected from the group consisting of fats, hydrogenated triglycerides and waxes that are solid or semi-solid at 20° C. and 1 atmosphere, the core contains 30% by weight to 97% by weight of matrix material based on the total mass of the core, the at least one volatile substance being contained in the core has a vapor pressure at 125° C. between 10 mm Hg and 200 mm Hg, a first coating layer is a non-confluent layer comprising at least one carrier material being attached to the core, the at least one carrier material is an inorganic material having a porous structure and a $D_{50}$ of 1 to 300 µm, and the core has an average surface coverage by the non-confluent layer of 1% to 50%; wherein the non-confluent layer contains at least one hydrophobic substance, and the particle is surrounded by at least one confluent layer and/or further non-confluent layer(s), and the presence of the first non-confluent layer increases the recovery of the volatile substance in the core during granulation or fluidization of the particle;

wherein the at least one volatile substance being contained in the core is selected from an essential oil or a plant extract each being prepared from a plant selected from the group consisting of oregano, thyme, caraway, mint, peppermint, anise, orange, lemon, fennel, star anise, clove, cinnamon, wintergreen and garlic; or from an ingredient, component or compound of the essential oil or plant extract selected from the group consisting of trans-anethole, D-limonene, γ-terpinene, p-cymene, 2-carene, linalool oxide, isomenthone, camphor, linalool, terpinen-4-ol, 2-isopropyl-1-methoxy-4-methylbenzene, L-menthol, ethylamine, α-terpineol, β-caryophyllene, D-carvone, methyl salicylate, α-caryophyllene, lavandulyl acetate, caryophyllene oxide, eugenol, thymol and carvacrol; and wherein the at least one matrix material is selected from hydrogenated palm oil, hydrogenated sunflower oil, hydrogenated corn oil, hydrogenated rapeseed oil, hydrogenated peanut oil, hydrogenated soybean oil, candelilla wax or carnauba wax.

2. The particle according to claim 1, wherein the core contains 3% by weight to 50% by weight volatile substances based on the total mass of the core.

3. The particle according to claim 1, wherein the at least one volatile substance being contained in the core has a vapor pressure at 125° C. between 30 mm Hg and 70 mm Hg.

4. The particle according to claim 1, wherein the core has a diameter between 50 µm and 1000 µm.

5. The particle according to claim 1, wherein the core contains 50% by weight to 85% by weight of matrix material based on the total mass of the core.

6. The particle according to claim 1, wherein the core includes the at least one texturizer and the at least one texturizer is selected from the group consisting of whey protein, corn protein, wheat protein, rape protein, pea protein, celluloses, starches, pectin, montmorillonites, stearates, sulphates and precipitated silica; wherein the at least one texturizer is up to 20% by weight of the at least one matrix material.

7. The particle according to claim 1, wherein the core has an average surface coverage by the non-confluent layer of 2% to 25%.

8. The particle according to claim 1, wherein the inorganic material has a porous structure with a $D_{50}$ of 2 to 150 µm.

9. The particle according to claim 1, wherein the carrier material of the non-confluent layer comprises at least one hydrophobic substance.

10. The particle according to claim 9, wherein the at least one hydrophobic substance in the non-confluent layer contains at least 100% by weight of the at least one semi-solid or liquid hydrophobic substance based on the mass of the carrier material without the at least one semi-solid or liquid hydrophobic substance.

11. The particle according to claim 9, wherein the at least one hydrophobic substance is selected from essential oils consisting of monoterpenes, α-terpinene, linalool, geraniol, menthol, citronellal, carvone or menthone; sesquiterpenes consisting of farnesol, farnesene, α-bisabolol or α-caryophyllene; or aromatic compounds consisting of carvacrol, thymol, cinnamaldehyde, anethole or eugenol.

12. The particle according to claim 1, wherein the particle is surrounded by at least one confluent layer.

13. A process for preparing a particle containing at least one volatile substance comprising the steps of:

forming a melt of an at least one matrix material, whereas the at least one matrix material is selected from the group consisting of fats, hydrogenated triglycerides and waxes that are solid or semi-solid at 20° C. and 1 atmosphere, wherein the at least one volatile substance has a vapor pressure at 125° C. of between 10 mm Hg and 200 mm Hg, forming a melt-mixture comprising an emulsion, dispersion, solution or suspension of the at least one volatile substance in the melt mixture, by incorporating the at least one volatile substance into the melt mixture, forming discrete cores of the melt mixture, wherein each of the cores contain 30% by weight to 97% by weight of the at least one matrix material based on the total mass of the core;

cooling the discrete cores, mixing the discrete cores with at least one carrier material containing at least one hydrophobic substance thereby forming a first non-confluent layer, wherein the at least one carrier material is an inorganic material having a porous structure and a $D_{50}$ of 1 to 300 µm, and surrounding the particle with at least one confluent layer and/or further non-confluent layer(s), wherein the presence of the first non-confluent layer increases the recovery of the at least one volatile substance in the core during granulation or fluidization of the particle.

14. The process according to claim 13, wherein in that the core is obtained by spray cooling.

15. The process according to claim 13, wherein the core material is mixed by shaking, slowly stirring or circulating in a batch container at a temperature of 20° C.±5° C. with at least one coating material wherein the at least one coating material is selected from hydrogenated palm oil, sunflower oil, corn oil, rapeseed oil, peanut oil, soybean oil, candelilla wax, carnauba wax, limonene, α-terpinene, linalool, geraniol, menthol, citronellal, carvone, menthone, farnesol, farnesene, α-bisabolol, α-caryophyllene, carvacrol, thymol, cinnamaldehyde, anethole, eugenol, starch, cyclodextrin, polyethylene glycol, carrageenan, alginates, gum arabicum, wheat gluten, chlorides, nitrates, phosphates, sodium sulphate or ammonium sulphate.

16. The process according to claim 13, wherein the confluent layer is applied by fluidized bed coating.

17. The particle according to claim 8, wherein the inorganic material has a porous structure with a $D_{50}$ of 5 to 30 µm.

* * * * *